(12) United States Patent
Lloyd et al.

(10) Patent No.: US 9,402,639 B2
(45) Date of Patent: Aug. 2, 2016

(54) METHOD AND APPARATUS FOR ALIGNMENT OF A MOBILE FLUOROSCOPIC IMAGING SYSTEM

(75) Inventors: Charles Frederick Lloyd, Reading, MA (US); Jon Thomas Lea, Hamstead, NH (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 2355 days.

(21) Appl. No.: 11/300,264

(22) Filed: Dec. 14, 2005

(65) Prior Publication Data

US 2007/0167698 A1    Jul. 19, 2007

(51) Int. Cl.
| | |
|---|---|
| A61B 5/05 | (2006.01) |
| A61B 17/17 | (2006.01) |
| A61B 6/00 | (2006.01) |
| A61B 5/055 | (2006.01) |
| A61B 5/11 | (2006.01) |
| A61B 8/00 | (2006.01) |

(52) U.S. Cl.
CPC ........... *A61B 17/1703* (2013.01); *A61B 6/4441* (2013.01); *A61B 6/547* (2013.01); *A61B 6/56* (2013.01); *A61B 17/1725* (2013.01); *A61B 5/055* (2013.01); *A61B 5/1127* (2013.01); *A61B 8/00* (2013.01); *A61B 17/1739* (2013.01)

(58) Field of Classification Search
None
See application file for complete search history.

(56) References Cited

U.S. PATENT DOCUMENTS

| | | | |
|---|---|---|---|
| 4,144,460 A | 3/1979 | Norman et al. | |
| 4,887,286 A | 12/1989 | Seidenberg et al. | |
| 5,113,424 A | 5/1992 | Burdea et al. | |
| 5,772,594 A * | 6/1998 | Barrick | 600/407 |
| 5,921,927 A * | 7/1999 | McArdle | 600/425 |
| 6,099,522 A * | 8/2000 | Knopp et al. | 606/10 |
| 6,131,690 A * | 10/2000 | Galando et al. | 180/411 |
| 6,425,865 B1 * | 7/2002 | Salcudean et al. | 600/437 |
| 6,470,207 B1 * | 10/2002 | Simon et al. | 600/426 |
| 6,728,599 B2 * | 4/2004 | Wang et al. | 700/258 |
| 6,782,287 B2 * | 8/2004 | Grzeszczuk et al. | 600/424 |
| 2002/0077540 A1 * | 6/2002 | Kienzle, III | 600/424 |
| 2003/0031291 A1 * | 2/2003 | Yamamoto et al. | 378/41 |
| 2003/0051733 A1 * | 3/2003 | Kotmel et al. | 128/207.14 |
| 2003/0099328 A1 * | 5/2003 | Jensen et al. | 378/198 |
| 2004/0076262 A1 | 4/2004 | Shao et al. | |
| 2004/0097806 A1 * | 5/2004 | Hunter et al. | 600/434 |
| 2004/0169673 A1 * | 9/2004 | Crampe et al. | 345/700 |

OTHER PUBLICATIONS

Hofsetetter et al (fluoroscopy as an imaging means for computer assisted surgical navigation).*

(Continued)

*Primary Examiner* — Joel F Brutus
(74) *Attorney, Agent, or Firm* — McAndrews, Held & Malloy, Ltd.; William Baxter

(57) ABSTRACT

A system and method for positioning a medical imaging unit is disclosed. The method may include accessing data from a plurality of sensors. The method may also include computing an optimal position for the medical imaging unit to acquire images of a point of interest. The computation may be based on data from plurality of sensors and information for calibrating the point of interest with at least one sensor. The method may also include computing instructions for manipulating the medical imaging unit from a first position to an optimal position. In an embodiment, the instructions may be displayed for a user to manually position the medical imaging unit. Alternatively, the instructions may be sent to an electric motor to position the medical imaging unit, or the electric motor may provide force feedback to guide a user to position the medical imaging unit in an optimal position.

21 Claims, 4 Drawing Sheets

(56) References Cited

OTHER PUBLICATIONS

French Patent Application No. FR0655518—Preliminary Search Report/Written Opinion Jun. 29, 2009 (5 pages).

State Intellectual Property Office, P.R. China, Office Action Application No. 200610130918.3 (7 pages) Nov. 20, 2009.

Hofstetter, R.; Slomczykowski, M.A.; Sati, M.; Nolte, L.-P.: *Fluoroscopy as an Imaging Means for Computer Assisted Surgical Navigation*, Comp. Aid. Surg., 4(2): 65-76, 1999.

* cited by examiner

METHOD AND APPARATUS FOR ALIGNMENT OF A MOBILE FLUOROSCOPIC IMAGING SYSTEM

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to a system and method for improved medical imaging. Particularly, the present invention relates to an improved navigation and visualization system and method for a mobile fluoroscopic imaging system.

Medical diagnostic imaging systems encompass a variety of imaging modalities, such as x-ray systems, computerized tomography (CT) systems, ultrasound systems, electron beam tomography (EBT) systems, magnetic resonance (MR) systems, and the like. Medical diagnostic imaging systems generate images of an object, such as a patient, for example, through exposure to an energy source, such as x-rays passing through a patient, for example. The generated images may be used for many purposes. For instance, internal defects in an object may be detected. Additionally, changes in internal structure or alignment may be determined. Fluid flow within an object may also be represented. Furthermore, the image may show the presence or absence of objects in an object. The information gained from medical diagnostic imaging has applications in many fields, including medicine and manufacturing.

One application for the use of medial diagnostic imaging systems is in the field computer assisted surgery. The field of computer assisted surgery generally encompasses the use of a computer or computer system during a surgical procedure. For example, a surgeon may wish to utilize a medical diagnostic imaging system to view a point of interest within the body during surgery. In general, during surgery a patient is generally kept stationary and a mobile imaging unit is manipulated into a position to acquire images of the point of interest. The manipulation of the mobile imaging unit is generally performed by a radiology technician, or other technician during surgery. The nurse or other technician generally positions the imaging unit in a position he thinks will provide the best image of the point of interest, then an image is acquired. Typically, the user does not get the positioning of the imaging unit optimal on the first try, so the user generally has to reposition the imaging unit, acquire another image, and assess the image to determine if the position of the imaging unit is optimal. A user generally goes through this iterative, trial-and-error process several times before the imaging unit is optimally positioned.

One problem with this trial-and-error positioning process is that it is time consuming and often difficult to execute. The entire surgical team generally waits for an optimal image before continuing with the surgery and it is often difficult to know how to move the C-arm simply by looking at the image. Even if one is able to read the images to move the C-arm correctly, the possibility of complications exists, as it does with most surgeries, and waiting for images during the surgery does not minimize potential complications. Moreover, each image exposes the patient and staff to radiation. The more images it takes to optimally position the imaging unit, the more radiation exposure the patient and the staff experience.

Accordingly, a need exists for a navigation and visualization system and method that is more efficient in positioning the imaging unit to acquire an optimal image. Such a system and method may allow the imaging unit to be positioned in a minimal amount of time and with a minimal amount of radiation exposure for both the patient and the staff.

SUMMARY OF THE INVENTION

Certain embodiments of the present invention include a method for positioning a medical imaging unit. The method includes accessing data from a plurality of sensors and computing an optimal position for the medical imaging unit to acquire images of a point of interest. The computation may be based on data from the plurality of sensors and information for calibrating the point of interest with at least one sensor. The method may further include the step of computing instructions for manipulating the medical imaging unit from a first position to the optimal position. The instructions may be displayed for a user to manually position the medical imaging unit in the optimal position. The step of displaying instructions includes providing feedback to the user regarding the current position of the medical imaging unit and the optimal position of the medical imaging unit. The instructions may also be used by an electric motor to position the medical imaging unit to the optimal position based on the instructions. Among other embodiments, the medical imaging unit may be a C-Arm or an ultrasound unit. The method may also include acquiring images of the point of interest. The point of interest may include screw holes as part of an intramedullary nail procedure. The point of interest may also include inlet and outlet images acquired as part of a pelvis procedure. The point of interest may also include a location of a catheter.

Certain embodiments of the present invention may include a system for positioning a medical imaging unit. The system may include a plurality of sensors for identifying the location of a plurality of reference points, a medical imaging unit for acquiring images, a computer unit for manipulating data, and a display unit for displaying information to a user. The computer unit may execute computer software for computing an optimal position for the medical imaging unit to acquire images of a point of interest, the computation being based on the location of the sensors. The computer unit may compute instructions for manipulating the medical imaging unit from a first position to the optimal position. The instructions may be displayed on the display unit for a user to manually position the medical imaging unit in the optimal position. The instructions may include providing feedback to the user regarding the current position of the medical imaging unit and the optimal position of the medical imaging unit.

The system may further include at least one electric motor. The instructions may be executed by the electric motor to position the medical imaging unit to the optimal position. The electric motor may provide force feedback for guiding a user to position the medical imaging unit in the optimal position. Among other embodiments, the medical imaging unit may be a C-Arm or an ultrasound unit.

Certain embodiments of the present invention may also include a computer-readable storage medium including a set of instructions for a computer. The set of instructions includes an accessing routine for accessing data from a plurality of sensors and a computation routine for computing an optimal position for the medical imaging unit to acquire images of a point of interest. The computation may be based on the data from the plurality of sensors and information for calibrating the point of interest with at least one sensor.

DETAILED DESCRIPTION OF THE INVENTION

Figure 1:
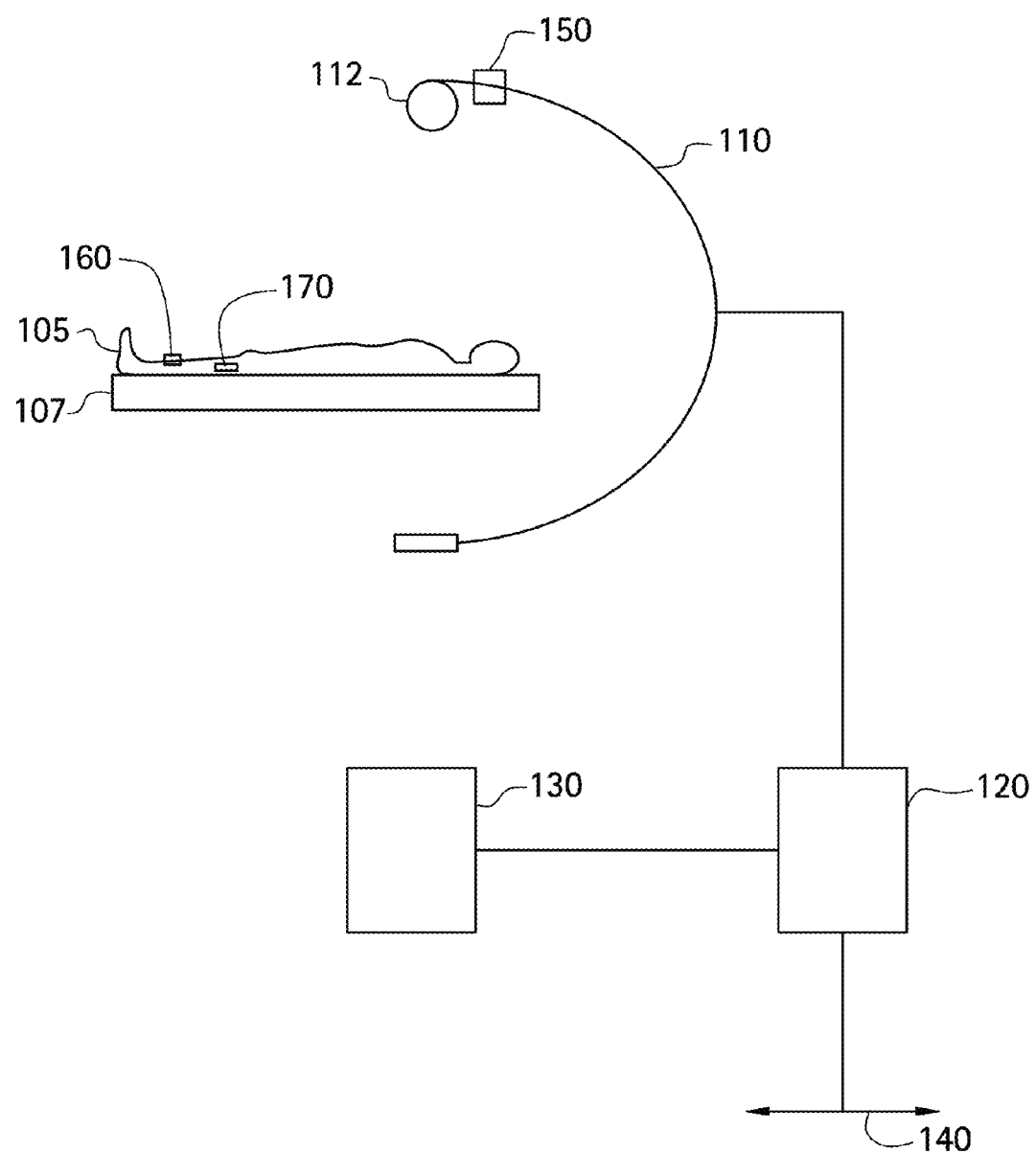
FIG. 1 illustrates an example of a system that may be used in accordance with an embodiment of the present invention.

FIG. 1 illustrates a system 100 for positioning a medical imaging unit in accordance with an embodiment of the present invention. The system 100 illustrates, as an example of a medical imaging unit, a C-arm unit 110. The medical imaging unit, however, may be other medical imaging equipment, such as an ultrasound unit, for example. Accordingly, any mobile medical imaging equipment may be used.

The C-arm unit 110 is connected to a computer unit 120. The connection between the C-arm unit 110 and the computer unit 120 may be wired or wireless. The computer unit 120 may be any equipment or software that permits electronic medical images, such as x-rays, ultrasound, CT, MRI, EBT, MR, or nuclear medicine for example, to be electronically acquired, stored, or transmitted for viewing and operation. The computer unit 120 may receive input from a user. The computer unit 120 represents, in general, equipment and software. The actual physical computer units may be separate units, part of a single unit, a computer system, or part of a computer system.

The computer unit 120 may be connected to other devices via an electronic network. The connection of the computer unit 120 to an electronic network is illustrated by line 140. The connection between the network 140 and the computer unit 120 may be wired or wireless. The computer unit 120 may also be connected to a display unit 130. The connection between the computer unit 120 and the display unit 130 may be wired or wireless. The display unit 130 may be a single display unit or multiple display units. Additionally, the display unit 130 may be a two-dimensional display unit or a three-dimensional display unit, for example. Accordingly, any display unit may be used in accordance with the present invention.

Element 105 represents a patient and element 107 represents a table on which the patient is lying. Elements 150, 160, and 170 are electronic sensors that may identify their location with reference to a reference frame and with reference to each other. Although three sensors 150-170 are shown, any number of sensors may be used. The sensors 150-170 are generally in electronic communication with the computer unit 120. The electronic communication may be over a wire or may be transmitted in a wireless fashion. The components of the system 100 may be single units, separate units, may be integrated in various forms, and may be implemented in hardware and/or in software.

In operation, the system 100 may be used to position the medical imaging unit 110. The sensors 150-170 may generally be positioned to create a reference frame. A reference frame may be created by having a reference sensor. The other sensors in the frame may identify their location in space in relation to the reference sensor.

Positioning of sensors is generally described in U.S. patent application Ser. No. 10/960,744 which is herein incorporated by reference. In the embodiment illustrated in the system 100, sensor 160 may be the reference sensor, sensor 150 may be the sensor identifying the location of the C-arm camera 112 in relation to the reference sensor, and sensor 170 may be the sensor identifying the location of the point of interest. In general, any number of sensors or any placement of sensors may be used.

The relationship between the location of the sensor 150 and the C-arm camera 112 is known by the computer unit 120. For example, if the sensor 150 is not placed on the C-arm camera 112, the computer unit 120 knows the distance and orientation. of the C-arm camera 112 to the sensor 150. Accordingly, the computer unit 120 may identify the location and orientation of the C-arm camera 112 in space.

Similarly, the relationship between the location of the sensor 170 and the point of interest is known by the computer unit 120. For example, if the sensor 170 is not placed at the point of interest, the computer unit 120 knows the distance of the point of interest to the sensor 170. Accordingly, the computer unit 120 may identify the point of interest in space.

In an embodiment, the reference sensor 160 may generally be positioned on a rigid part of the anatomy of the patient, for example a bone. Sensors 150 and 170 may identify their position in space with relation to sensor 160, and thus sensors 150 and 170 may identify their position with relation to each other. As illustrated in the system 100, sensor 150 may be attached to the C-arm camera 112. Sensor 170 may identify the location of the point of interest. The location of the sensors 150-170 may be communicated to the computer unit 120. The computer unit 120 may then compute the optimal position of the C-arm camera 112 to acquire images of the point of interest. The computer unit 120 may make the computation based on the location of the sensors 150, 160, and 170.

Once the computer unit 120 computes the optimal position of the C-arm camera 112, the computer unit 120 may compute instructions on how to manipulate the C-arm to locate the C-arm camera 112 in the optimal position. In an embodiment, the instructions may be displayed on the display unit 130 and the user may manually position the medical imaging unit 110 in the optimal position. Alternatively, the instructions may be displayed on the medical imaging unit 110, for example using positioning indicators, such as LEDs, to instruct the user. For example, the instructions may be displayed in the form of arrows directing the user to which direction to manipulate the medical imaging unit. The displayed instructions may include feedback to the user regarding the current position of the medical imaging unit and the optimal position of the medical imaging unit. For example, the user may move the medical imaging unit, and the computer unit 120 may observe the move in location. The computer unit 120 may re-compute the instructions and display new directional information to the user. This iterative process may be repeated until the medical imaging unit is positioned in the optimal position, wherein an indicator may be displayed to the user that the medical imaging unit is in the optimal position. Alternatively, the instructions may be sent to an electric motor, and the electric motor may position the medical imaging unit in the optimal position. Once the medical imaging unit 110 in optimal position, an image may be acquired. Accordingly, instead of using a trial-and-error technique to position the medical imaging unit and exposing the patient and staff to unnecessary radiation, the system 100 allows a more efficient capture of images while minimizing exposure to radiation.

Figure 2:
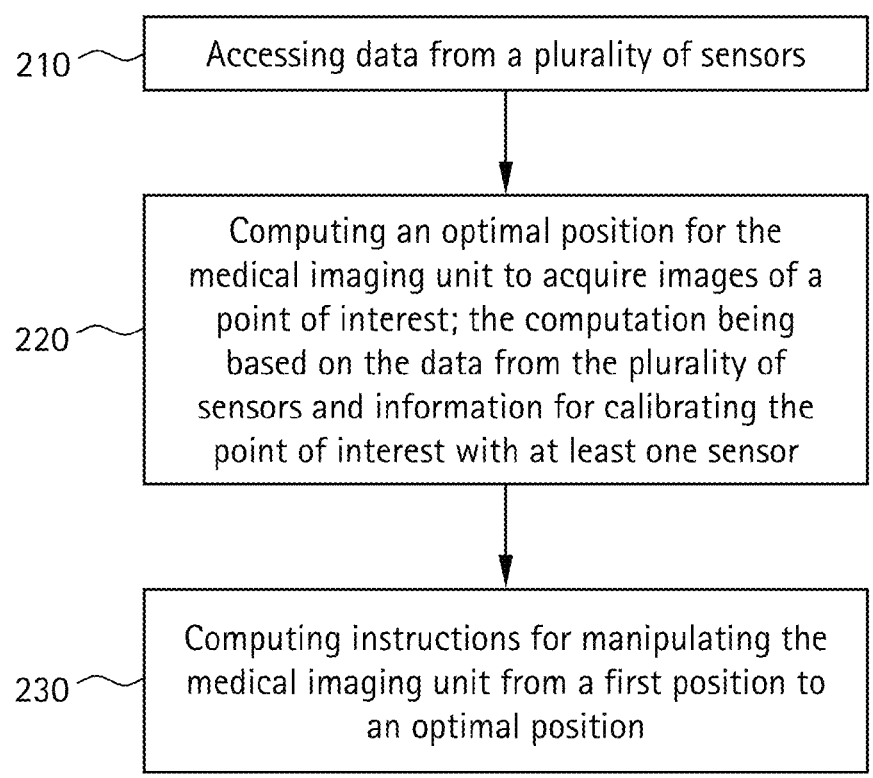
FIG. 2 illustrate a method that may be used in accordance with an embodiment of the present invention.

FIG. 2 illustrates a method 200 that may be used in accordance with an embodiment of the present invention. The method 200 may be performed by the computer unit 110 of the system 100 or other associated computer system or equipment. The method 200 includes, at step 210, accessing data from a plurality of sensors. The data may include the relative position of the sensors as part of the reference frame. The data may also include calibration information. The calibration information may include the position of the point of interest sensor with respect to the point of interest. Also, the calibration information may include the position of, for example, the C-arm camera sensor with respect to the C-arm camera.

At step 220, an optimal position for the medical imaging unit to acquire an image of a point of interest may be computed. The computation may be based on the data from the sensors. The data from the sensors may indicate the position of the sensors. The computation may also include information for calibrating the point of interest with at least one sensor. The information for calibrating the point of interest with at least on sensor may include the position of the point of interest sensor with respect to the point of interest.

At step 230, instructions may be computed for manipulating the medical imaging unit from a current position to an optimal position. In an embodiment, the instructions may be displayed for a user to manually position the medical imaging unit in the optimal position. The displayed instructions may include visual feedback to the user regarding the current position of the medical imaging unit and the optimal position of the medical imaging unit. For example, the user may move the medical imaging unit. The computer unit may observe the move in location. The computer unit may re-compute the instructions and display new directional information to the user. This iterative process may be repeated until the medical imaging unit is positioned in the optimal position as is indicated in the method 200 by the arrow from step 230 to step 210.

Alternatively, the instructions may be sent to an electric motor, and the electric motor may position the medical imaging unit in the optimal position. Once the medical imaging unit is in optimal position, an image may be acquired. In another alternative, the instructions may be sent to an electric motor and used to provide force feedback to guide a user to position the medical imaging unit in the optimal position. To a user, it would feel like the C-Arm was moving itself into the optimal position as the user pushed the C-Arm. Such force feedback may be useful rather than having electric motors move automatically. Such automatic movement may snag tubes, catheters, and cables, for example, that may be attached to the patient.

Figure 3:
FIG. 3 illustrates an example of an embodiment of the present invention.

FIG. 3 illustrates an example of an application of the above described system and method. In an intramedullary nail procedure (IM Nail) a deformable nail is placed down the axis of the femur and secured with a number of screws. FIG. 3 illustrates the screw holes 310 as located in the body cavity. A method such as described in U.S. Publication No. 2002/0077541, which is herein incorporated by reference, may be used to locate the deformed locations of the screw holes. In an embodiment, a sensor, such as sensor 160 may be placed on a rigid anatomical structure, such as a bone of the patient. A sensor, such as sensor 170 may be attached to the end of the deformable nail away from the screw holes. The distance the sensor is placed from the screw holes may be determined, however, and the distance and orientation of the screw holes from the sensor 170 may be determined.

Given the position and orientation of the screw holes, a C-arm with an attached tracking system as described above may be optimally positioned to take an image through the center of the screw holes. The pre-computed C-arm calibration of the relationship of the location of the sensor 170 with respect to the location of the screw holes gives the projective alignment of the medical imaging unit with respect to the tracking system. The location and orientation of the screw holes specifies an appropriate line along which to center the C-arm camera. The system may then provide visual alignment cues, or with a motorized system as described above, to optimally position the medical imaging unit.

Figure 4:
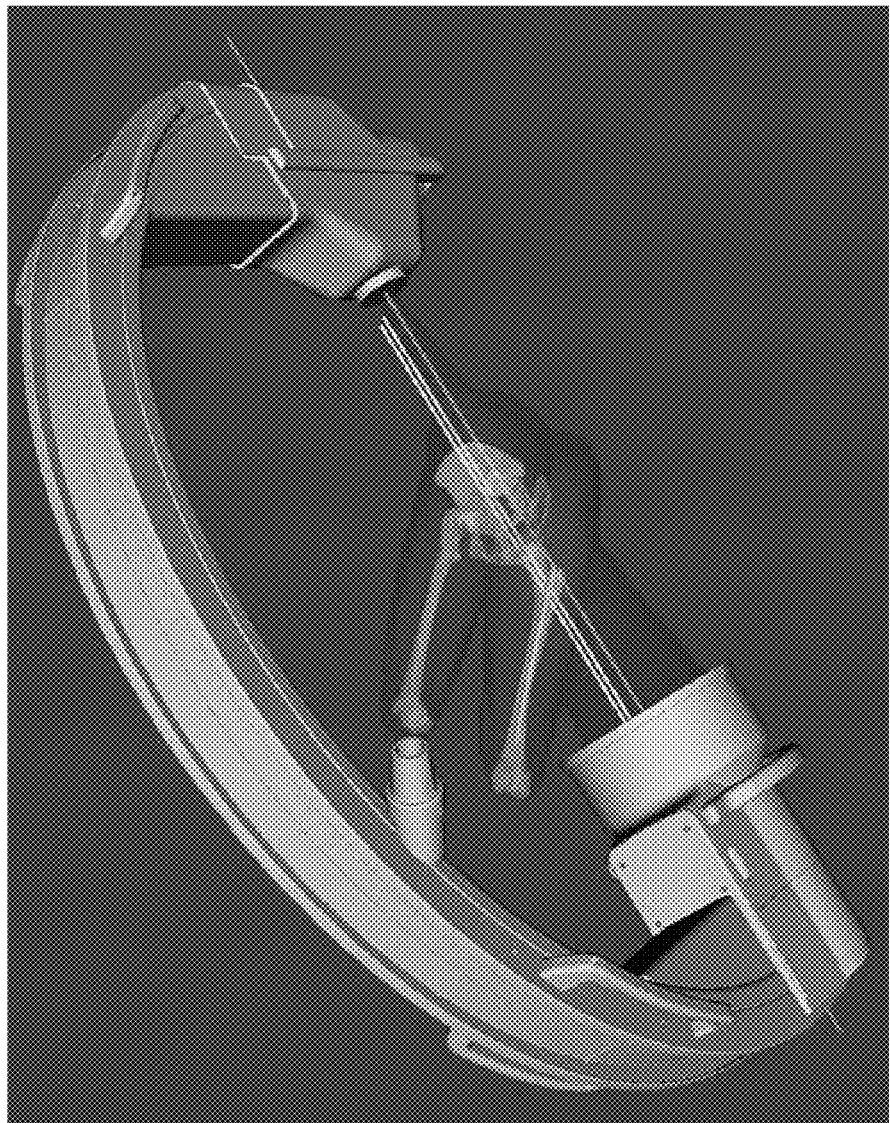
FIG. 4 illustrates an example of an embodiment of the present invention.

FIG. 4 illustrates an example of an application of the above described system and method. In performing a pelvis procedure, it is difficult to obtain a good inlet and a good outlet view. In an embodiment, a sensor, such as sensor 160 may be placed external to the body on a bony reference point. Such placement may require touching (or palpating) several external fiducially points of the body with an instrument attached to sensor 160. A sensor, such as sensor 170, may be placed accordingly to obtain inlet and outlet images. Using the tracking system and method as described above, the reference points may guide the position of the C-arm to an optimal position for both inlet and outlet images. FIG. 4 illustrates utilizing a C-arm to acquire an image using a tracking system and method as described above.

In another example of an application of the above describe system and method, while inserting a catheter into a patient's artery, it may be difficult to know where the tip of the catheter is located. In an embodiment, if the tip of the catheter has a sensor, such as sensor 170, the tip location may be monitored. Additionally, the tip location may be used to help position a C-arm unit to monitor the progress of the catheter insertion without having to perform multiple shots to try and find the catheter.

The system and method described above may be carried out as part of a computer-readable storage medium including a set of instructions for a computer. The set of instructions includes an accessing routine for accessing data from a plurality of sensors. The set of instructions also includes a computation routine for computing an optimal position for the medical imaging unit to acquire images of a point of interest. The computation may be based on the data from the plurality of sensors and information for calibrating the point of interest with at least one sensor. The set of instructions may also include an instruction routine for computing instructions for manipulating the medical imaging unit from a first position to an optimal position.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for positioning a mobile fluoroscopic imaging system, the method comprising:
    positioning a first sensor on the mobile fluoroscopic imaging system;
    positioning a second sensor to identify a location and an orientation of a point of interest of a patient;
    electronically communicating data from the first sensor and the second sensor to a computer unit;

determining, by the computer unit, a location of the point of interest and an initial location of the mobile fluoroscopic imaging system according to the data;
computing, by the computer unit, an optimal position of the mobile fluoroscopic imaging system to acquire at least one image of the point of interest of the patient according to the location and the orientation of the point of interest of the patient;
computing, by the computer unit, instructions for manually moving the mobile fluoroscopic imaging system from the initial location to the optimal position; and
displaying the instructions for manually moving the mobile fluoroscopic imaging system from the initial location to the optimal position.

2. The method of claim 1, further comprising providing feedback regarding a current position and the optimal position of the mobile fluoroscopic imaging system.

3. The method of claim 1, further comprising controlling an electric motor to move the mobile fluoroscopic imaging system to the optimal position according to the instructions.

4. The method of claim 1, wherein the point of interest of the patient includes screw holes for an intramedullary nail procedure.

5. The method of claim 1, wherein the at least one image of the point of interest of the patient includes an inlet image and an outlet image acquired according to a pelvis procedure.

6. The method of claim 1, wherein the point of interest of the patient includes a catheter.

7. The method of claim 1, wherein the instructions are further computed according to calibration information.

8. The method of claim 1, further comprising manually moving the mobile fluoroscopic imaging system into the optimal position.

9. The method of claim 1, further comprising using positioning indicators for moving the mobile fluoroscopic imaging system into the optimal position.

10. The method of claim 9, wherein the positioning indicators include arrows.

11. The method of claim 1, further comprising:
positioning a third sensor on the patient to create a reference frame with the first sensor and the second sensor; and
wherein said computing an optimal position further comprises computing the optimal position of the mobile fluoroscopic imaging system according to the reference frame.

12. A system for positioning a mobile fluoroscopic imaging system, the system comprising:
a first sensor configured to electronically communicate data to a computer unit to identify an initial location of the mobile fluoroscopic imaging system;
a second sensor configured to electronically communicate data to identify a location and an orientation of a point of interest of a patient;
a computer unit configured to:
compute an optimal position for the mobile fluoroscopic imaging system to acquire at least one image of the point of interest of the patient according to the location and the orientation of the point of interest of the patient, and
compute instructions for manually moving the medical imaging unit from the initial location to the optimal position; and
a display configured to display the instructions for manually moving the medical imaging unit from the initial location to the optimal position.

13. The system of claim 12, wherein the instructions comprise feedback regarding a current position and the optimal position of the mobile fluoroscopic imaging system.

14. The system of claim 12, further comprising an electric motor configured to move the mobile fluoroscopic imaging system into the optimal position according to at least a portion of the instructions.

15. The system of claim 14, wherein the electric motor is configured to provide force feedback for guiding the mobile fluoroscopic imaging system into the optimal position.

16. The system of claim 12, wherein the display is further configured to display positioning indicators to instruct how to move the mobile fluoroscopic imaging system into the optimal position.

17. The system of claim 16, wherein the positioning indicators include arrows.

18. The system of claim 12, wherein the instructions comprise instructions for manually moving the mobile fluoroscopic imaging system into the optimal position.

19. A non-transitory computer-readable storage medium including a set of instructions for a computer, the set of instructions comprising:
a reception routine for receiving, at a computer unit, electronic data communicated from a first sensor on a mobile fluoroscopic imaging system and a second sensor on a patient having a point of interest;
a determination routine for determining, by the computer unit, a location and an orientation of the point of interest and an initial location of the mobile fluoroscopic imaging system according to the electronic data;
a computation routine for computing, by the computer unit, an optimal position of the mobile fluoroscopic imaging system to acquire at least one image of the point of interest of the patient according to the location and the orientation of the point of interest of the patient;
a computation routine for computing, by the computer unit, instructions for manually positioning the mobile fluoroscopic imaging system from the initial location to the optimal position; and
a display routine for displaying the instructions for manually positioning the mobile fluoroscopic imaging system from the initial location to the optimal position.

20. The set of instructions of claim 19, further comprising a display routine for displaying positioning indicators to instruct how to move the mobile fluoroscopic imaging system into the optimal position.

21. The set of instructions of claim 20, wherein the positioning indicators include arrows.

* * * * *